(12) United States Patent
Liptay et al.

(10) Patent No.: US 9,220,270 B2
(45) Date of Patent: Dec. 29, 2015

(54) METHODS FOR APPLYING DIFORMYLUREA TO CROPS FOR GREATER PLANT PRODUCTIVITY

(71) Applicant: Stoller Enterprises, Inc., Houston, TX (US)

(72) Inventors: Albert Liptay, Houston, TX (US); Jerry Stoller, Houston, TX (US)

(73) Assignee: Stoller Enterprises, Inc., Houston, TX (US)

( * ) Notice: Subject to any disclaimer, the term of this patent is extended or adjusted under 35 U.S.C. 154(b) by 0 days.

(21) Appl. No.: 14/560,990

(22) Filed: Dec. 4, 2014

(65) Prior Publication Data

US 2015/0150261 A1   Jun. 4, 2015

Related U.S. Application Data

(60) Provisional application No. 61/911,909, filed on Dec. 4, 2013.

(51) Int. Cl.
*A01N 25/26* (2006.01)
*A01N 47/34* (2006.01)

(52) U.S. Cl.
CPC ...................... *A01N 47/34* (2013.01)

(58) Field of Classification Search
None
See application file for complete search history.

(56) References Cited

U.S. PATENT DOCUMENTS

| 6,040,273 | A | 3/2000 | Dean |
| 6,448,440 | B1 | 9/2002 | Dean |
| 6,710,085 | B2 | 3/2004 | Dean |
| 2011/0300110 | A1 | 12/2011 | Hungenberg et al. |
| 2012/0255475 | A1 | 10/2012 | Mariman et al. |
| 2013/0072384 | A1 | 3/2013 | Pohlman et al. |
| 2013/0116119 | A1 | 5/2013 | Rees et al. |
| 2013/0232646 | A1 | 9/2013 | Baum et al. |

OTHER PUBLICATIONS

PCT International Search Report & Written Opinion (PCT/US2014/068619), dated Mar. 3, 2015.

*Primary Examiner* — Alton Pryor
(74) *Attorney, Agent, or Firm* — Yancy IP Law, PLLC

(57) ABSTRACT

It has been discovered that applying diformylurea (DFU) to seed of crop plants enhances the feeder root capability of the plants to take up water and minerals from the soil environment. A further discovery is that crop plant cellular water and soil maintenance around feeder roots is increased by applying DFU to crop seeds prior to planting, to the soil surrounding the plants or to foliage of the plants. A still further discovery is that crop plant drowning is prevented when flooded by excessive rain or other types of flooding. A still further discovery is that crop plant yields are enhanced by combining DFU and nitrogen fertilizer to the soil of the crop plants.

3 Claims, 15 Drawing Sheets
(15 of 15 Drawing Sheet(s) Filed in Color)

METHODS FOR APPLYING DIFORMYLUREA TO CROPS FOR GREATER PLANT PRODUCTIVITY

BENEFIT OF FILING DATE OF PROVISIONAL APPLICATION

This application claims priority of Dec. 4, 2013 from Provisional Application 61/911,909.

BACKGROUND OF THE INVENTION (1) Field of the Invention

This invention relates to new methods for enhancing the crop production by application of diformylurea (DFU) to crops.

(2) Description of Prior Art

Previous U.S. patents (U.S. Pat. No. 6,040,273, U.S. Pat. No. 6,448,440, U.S. Pat. No. 6,710,085) to Dean have described the beneficial effects of DFU applied to crop plants to enhance the rate of seed germination and seedling growth of a number of crop plant variables such as shoot and root fresh weights.

IDENTIFICATION OF OBJECTS OF THE INVENTION

An important object of this invention is to apply DFU to achieve larger increases in the functional capacity of a crop plant root system to achieve selective root tissue synthesis resulting in more and effective feeder roots that can take up water and minerals from soil in contrast to thicker roots with less root tips for water and nutrient uptake from soil that are part of the heterogeneous overall root mass.

Another object of the invention is to apply DFU to crop plants to enhance crop plant cellular water and soil moisture around feeder roots.

Another object of the invention is to apply DFU to crop plants subject to flooding of the fields in which they are planted to prevent drowning of the plants in flooded fields.

Another object of the invention is to apply DFU to crop plants to enhance crop plant growth and productivity while not suppressing the effect of pesticides, herbicides or fungicides.

SUMMARY OF THE INVENTION

The method of DFU treatment of crop plant tissue of the invention includes exogenous treatment of the crop plants with a DFU solution at a rate of between 0.1 to 10 pints/acre over the crop growth stages or as a preferred rate of DFU at 0.5 to 1.5 pints per acre.

The method of exogenous treatment of the crop plants can be achieved as foliar treatments after the first or second leaf has formed or later in the growing season of the crop plant (with repeated [preferred] or single applications) over the canopy (leaves) at rates from 2 to 16 ounces of DFU per acre of crop per individual application or applied as repetitive applications over the whole crop growing season of up to 10 pints/acre.

The treatment of crop plants includes "in furrow" treatment at crop planting onto the seed and onto the soil in the opened sowing furrow at the rates of between 0.1 to 10 pints/acre, with a preferred rate of 0.5 to 1.5 pints per acre applied as an in furrow application.

As a method of preferred treatment, exogenous DFU is applied in furrow at a rate between 0.1 to 10 pints/acre but with a preferred rate of 0.5 pints/acre to 1.5 pints/acre as a spray of the "opened" soil furrow, wherein the seed of the crop plant is first sown and the spray of the DFU solution then covers both the seed and the soil in the "opened" furrow, before closure of the furrow and subsequent compression of the soil over the closed furrow for an important and appropriate closed "soil" contact with the seed for optimal seed germination and growth of the crop plant seedling.

A preferred time for such application as above is immediately at the time of sowing of the crop seed.

DFU applications throughout the growing season of the crop, can be made as foliar or "in-soil" applications at the rates of 2 to 16 ounces per acre. The DFU applications are always more effective if additional water is applied with the DFU at rates between 5 to 25 gallons of water per acre.

BRIEF DESCRIPTION OF THE DRAWINGS

The patent or application file contains at least one drawing/photograph executed in color. Copies of this patent or patent application publication with color drawings/photographs will be provided by the Office upon request and payment of the necessary fee.

DESCRIPTION OF THE INVENTION

Figure 1:
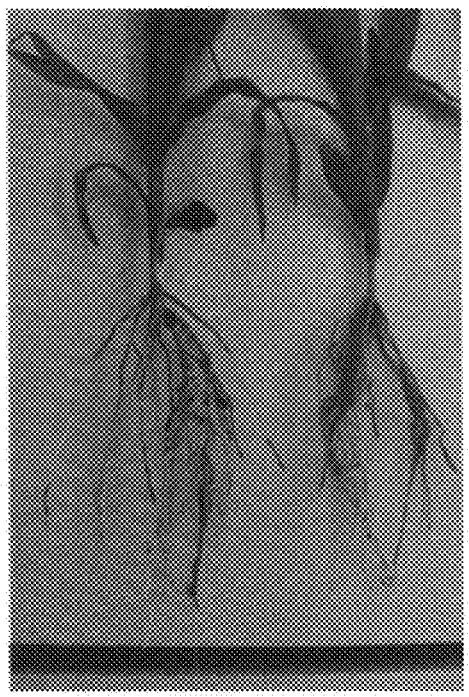
FIG. 1 is a photograph illustrating root structure of two corn plants, one treated (on right) with DFU, the other untreated (on left)

It has been discovered that application of DFU to growing crop plants results in a large increase in the functional capacity of the crop plant root system because of selective root tissue synthesis and development of fine small feeder roots that operate to take up water and minerals from the soil environment. Treatment of crop plant tissue described herein includes exogenous treatment of the crop plants with a DFU solution at a rate of between 0.1 to 10 pints/acre over the crop growth stages or as a preferred rate of 0.5 to 1.5 pints per acre. Preferably, the concentration of the DFU which is applied at the above rates is from stock solutions of 0.001 Molar to 1.0 Molar with a preferred Molarity of 0.001 Molar to 0.05 Molar. FIG. 1 is a photograph of two plants: the plant on the left had no treatment with DFU; the plant on the right hand side was treated with DFU. The treated plant on the right hand side has a significantly greater fine small feeder root system development than does the untreated plant on the left hand side. The treated plant on the right hand side of FIG. 1 is in contrast to the thicker deeper roots of the plant on the left hand side which has fewer "root tips" for water and nutrient uptake from the soil. The DFU treated plant on the right has smaller feeder roots for water, mineral, and nutrient uptake from the roots to the shoots.

Figure 2:
FIG. 2 is a photograph of a root structure showing dry soil around the roots of a corn plant that has not been treated with DFU.
Figure 3:
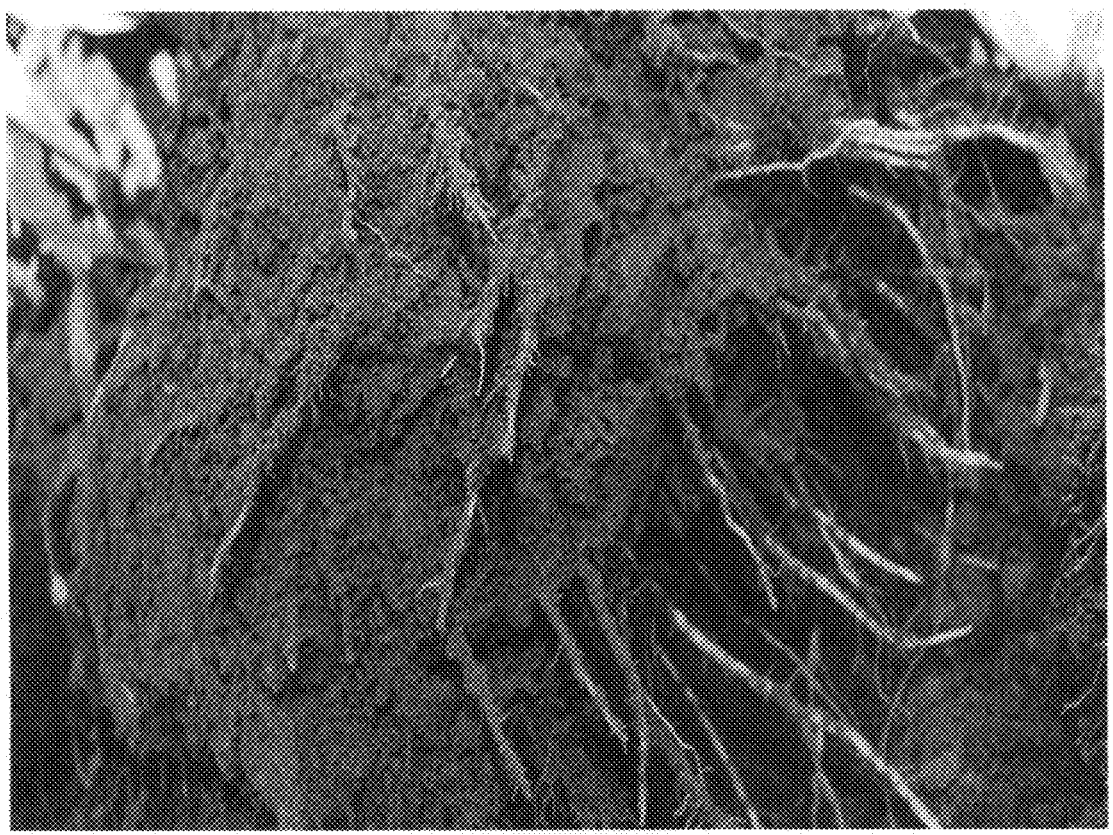
FIG. 3 is a photograph of a root structure showing moist soil around the roots of a corn plant (grown under the same conditions as that of FIG. 2) treated with DFU.

It has also been discovered that applying DFU to crop plants causes enhancement of crop plant cellular water and soil moisture around the feeder roots. Compare the feeder root system of FIG. 2 of a plant that has had no DFU applied to it with the feeder root system of FIG. 3 of a plant that has DFU applied to it. Much more moist soil can be seen around the root system of FIG. 3.

The method of applying DFU to crop plants, which has been covered by natural rain or other types of flooding is a distinctive enhanced feature of DFU treatment of crop plants to ameliorate damaging effects of field soil excessive moisture such as flooding. The most efficacious method of DFU treatment for this feature is that of an "in furrow" application into the open soil furrow at time of crop seed sowing with a spray of DFU at a dose of one to one and a half pints per acre over the seed and unto the soil of the open furrow before closure of the open furrow and application of pressure to the closed furrow for optimal soil contact with the seed.

Figure 4:
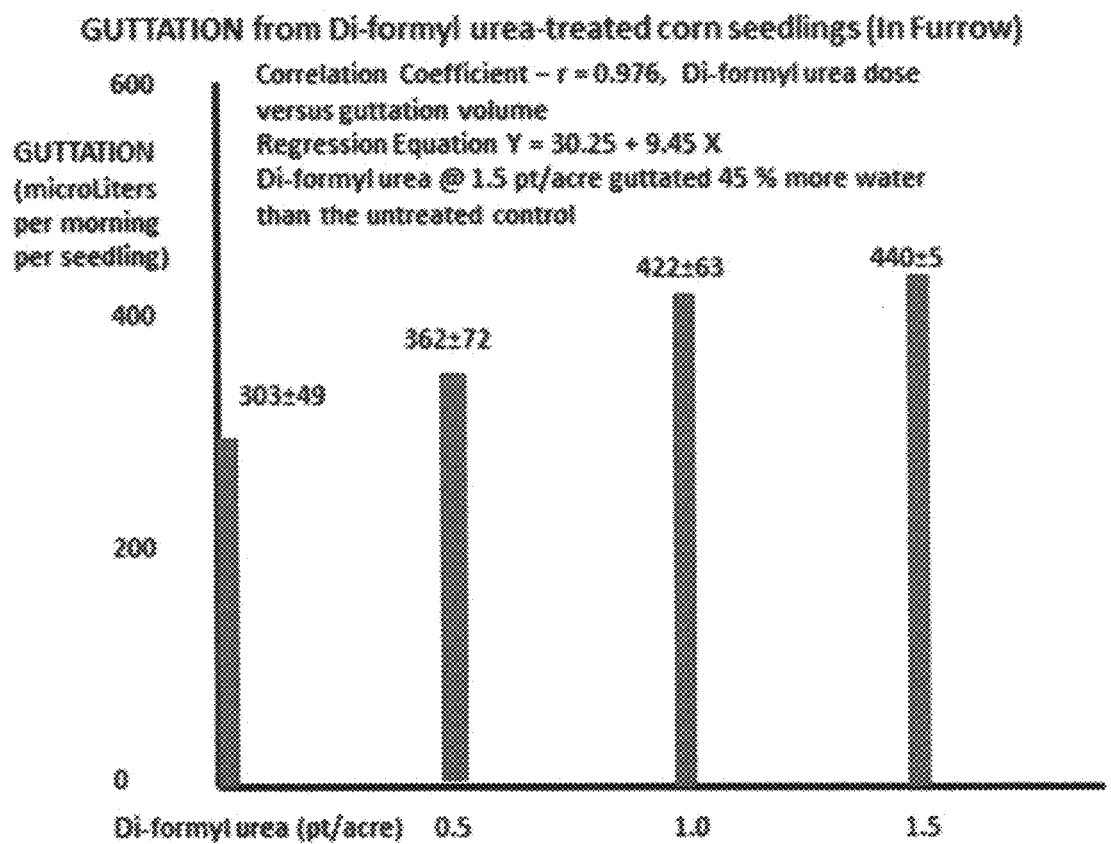
FIG. 4 is a graph which illustrates increase in guttation of DFU corn seedlings as a function of DFU application.

It has also been discovered that treatment of crop plants such as corn increases guttation of the water on plant leaves. FIG. 4 illustrates the results of increased guttation on seedling leaves as a function of DFU amounts.

It has been further discovered that applying DFU to crop plants prevents drowning of the plants when a crop field is flooded by excessive rain or other types of flooding. The most effective method of DFU treatment to prevent drowning is that of an in furrow application of DFU open soil furrow at the time of crop seed sowing. DFU is preferably sprayed at a dose of 1 pint per acre to 1½ pints per acre over the seed and onto the soil of the open furrow before closure of the open furrow and application of pressure to the closed furrow for optional soil contact with the seed.

Figure 5:
FIG. 5 is a photograph of a field of corn plants that has been flooded by excessive rain.
Figure 6:
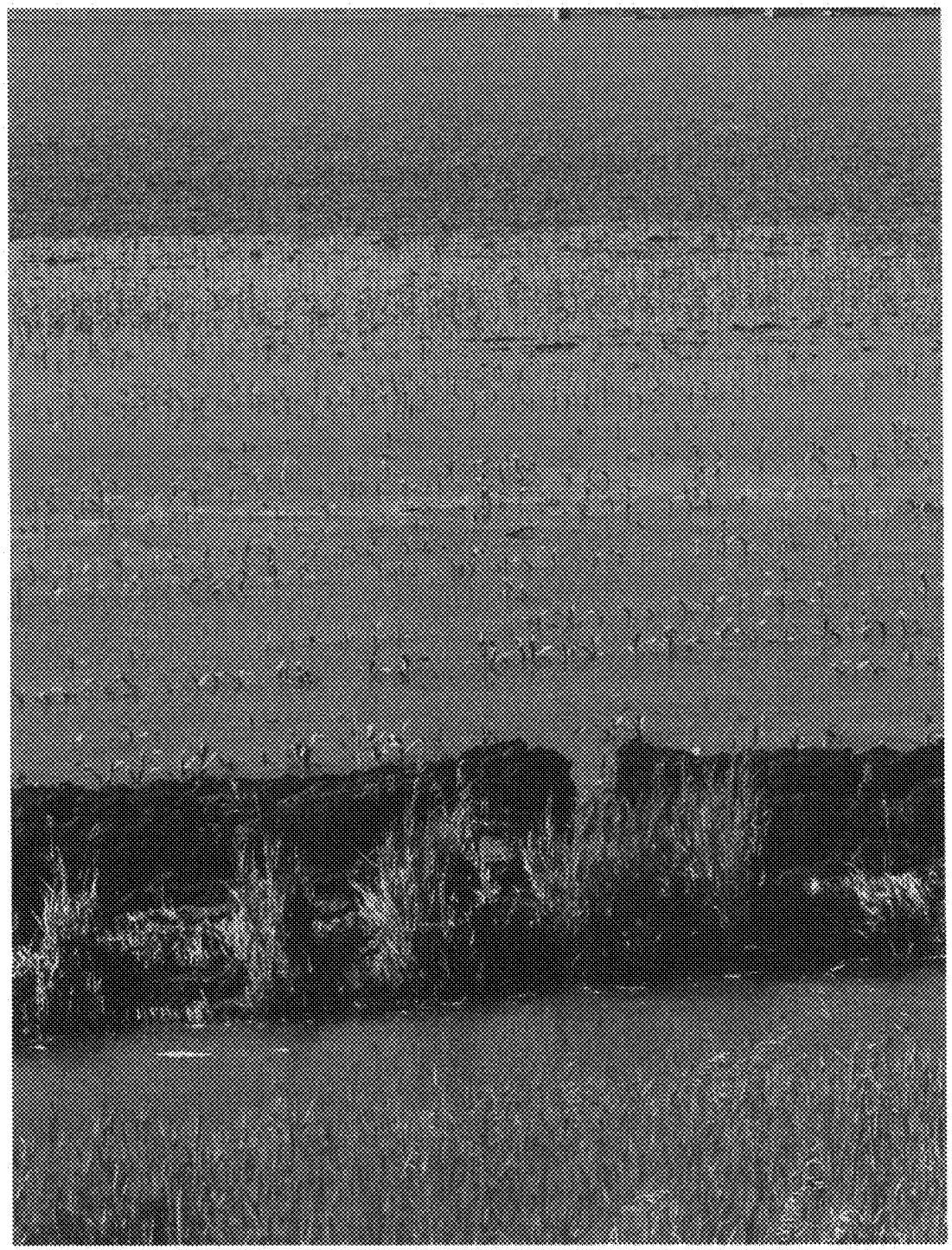
FIG. 6 is a photograph of the field of FIG. 5 after water has partially receded, but showing corn plants that had been treated with DFU alive in the water.
Figure 7:
FIG. 7 is a close-up photograph showing a DFU treated corn plant of FIG. 6.
Figure 8:
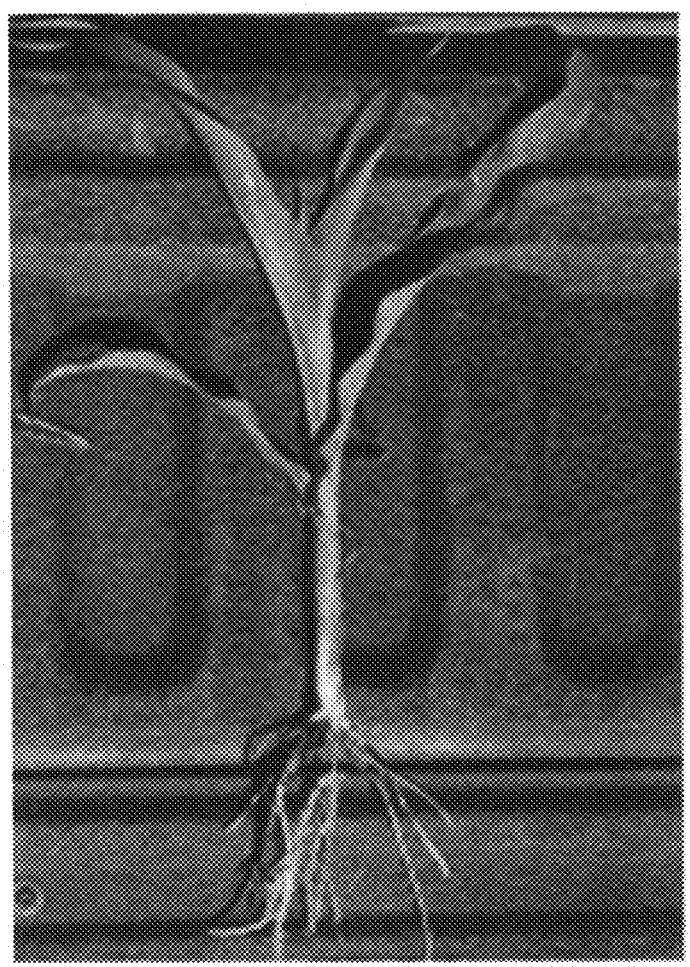
FIG. 8 is a photograph of a DFU treated corn plant that survived the flood of FIG. 5.
Figure 9:
FIG. 9 is a photograph of corn plants that were not treated with DFU after flooding has receded.
Figure 10:
FIG. 10 is a close-up photograph of non-DFU treated corn plants after having experienced a flooding condition.
Figure 11:
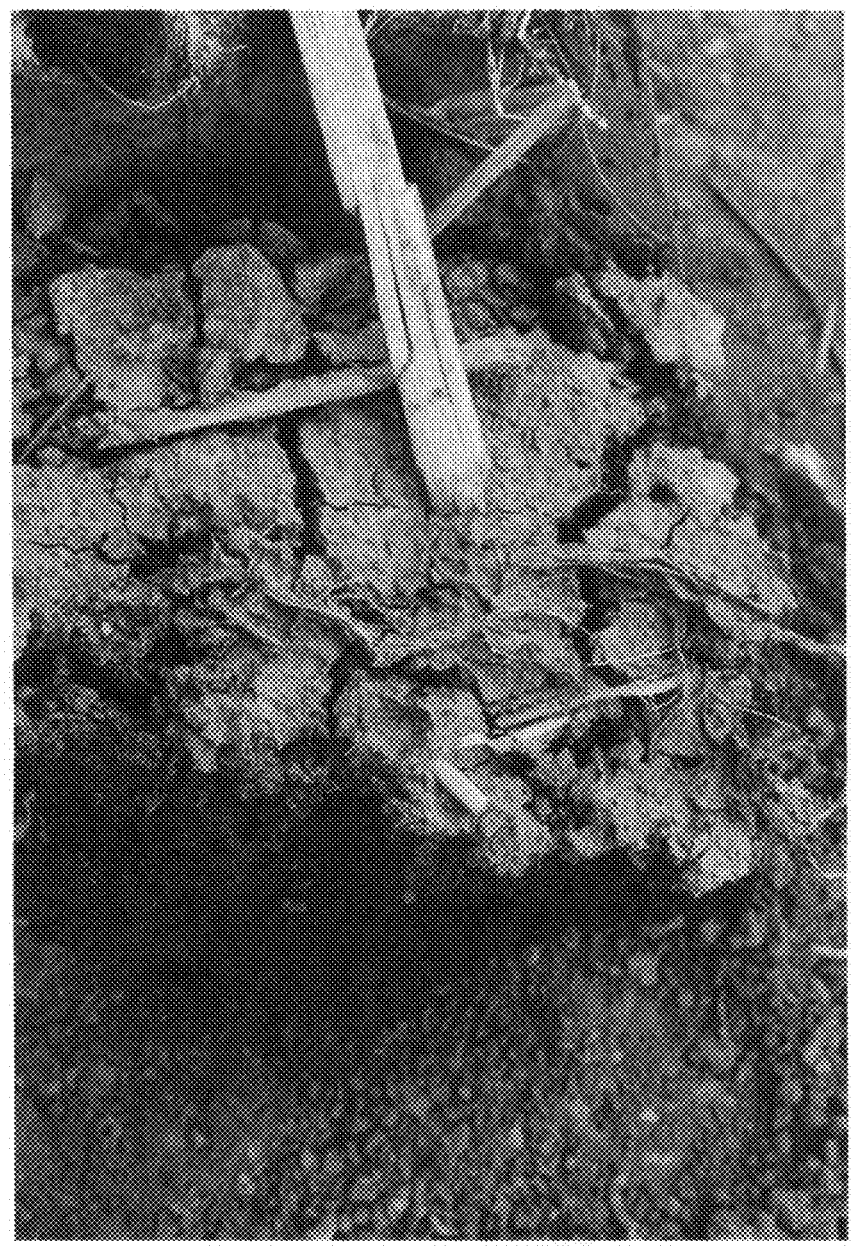
FIG. 11 is a close-up photograph of a dead corn plant (that was not treated with DFU) after flooding.
Figure 12:
FIG. 12 is another photograph of corn plants that were treated with DFU that survived flooding.
Figure 13:
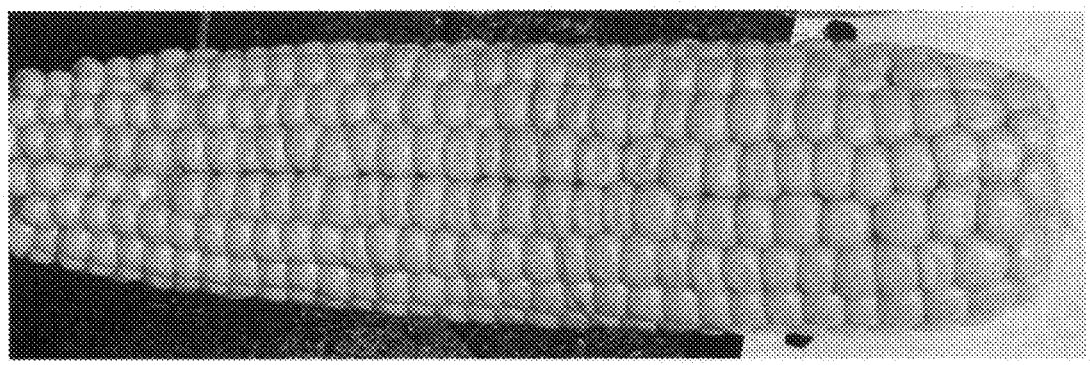
FIG. 13 is a photograph of a corn cob of a plant that survived the flood of FIG. 5.

FIG. 5 is a photograph of a corn field completely flooded by excessive rain. FIGS. 6 and 7 show corn plants treated with DFU after the excessive water has retreated somewhat. The corn plants are seen to be growing. FIG. 8 is a photograph of a corn plant that is seen to have survived the flood. FIG. 9 is a photograph of a corn field which has not been treated with DFU, but after flooding, has been almost completely killed because of the water. FIG. 10 is a close-up photo of corn that has been killed because of flooding. FIG. 11 is a photo of the remains of a corn plant that has been killed by the flooding. FIG. 12 is a photo of the corn plants treated with DFU with the plants growing in excessive moisture. FIG. 13 is a photo of a corn cob of a corn plant that was treated with DFU and flooded as in FIGS. 5, 6 and 7.

It has also been discovered that DFU treatment of corn plants increases the inter-nodal volume of corn plants. Table 1 below confirms that discovery where intermodal stalk volumes of untreated corn crop plants was calculated to be 311.71 cc per plant whereas the inter-nodal stalk volumes of the DFU-treated corn plant was 355.47, an increase of 14% over the control plant.

TABLE 1

| Growth Stage | Internodal Volume (cc) Untreated corn plant | Internodal Volume (cc) DFU-Treated corn plant |
| --- | --- | --- |
| V1 | 26.93 | 33.49 |
| V2 | 41.2 | 45.02 |
| V3 | 46.9 | 55.76 |
| V4 | 52.06 | 59.14 |
| V5 | 48.38 | 54.34 |
| V6 | 42.21 | 47.79 |
| V7 | 31.26 | 35.02 |
| V8 | 22.77 | 24.9 |

Figure 14:
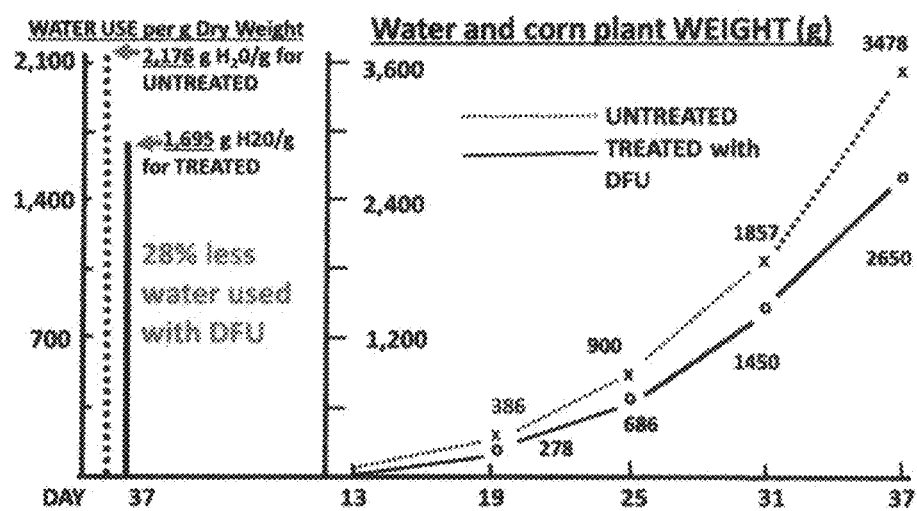
FIG. 14 is a graph showing the effect of DFU treatment on corn plants thereby requiring less water use for growing.

It has also been discovered that crops treated with DFU require less water for growing. See the results illustrated in FIG. 14. In two barrels that were sealed at the top, a precise amount of growing medium was added with appropriate fertilizer and a precise amount of water. One of the barrels had fertilizer only while the second had a 0.0015% solution of DFU. Seven corn seedlings were germinated and grown in the growing medium in each of the barrels for a period of 37 days. At 37 days the fresh weight and dry weights of corn plants were determined. The graph on the right side of FIG. 4 depicts the combined weight of the water and the plants growing out of the barrels. The graph on the left depicts the average amount of water needed to grow the treated vs the untreated corn, indicating a twenty eight percent savings with the DFU-treated plants contrasted to the untreated plants. The two barrels were constantly weighed electronically.

As further evidence the increase in crop production as a result of DFU treatment see Table 2 below. Untreated soybean plant yields were 52.5 bushels per acre. The DFU treated soybean plants yielded 111 bushels per acre. This represents an increase in water use efficiency of 111 percent.

TABLE 2

| Treatment | Average Yield bu per acre | Standard Deviation | T test vs control P = % | Rep 1 Yield | Rep2 Yield | Rep3 Yield | Rep4 Yield |
| --- | --- | --- | --- | --- | --- | --- | --- |
| Control Untreated | 52.5 | 1.68 | | 60 | 54 | 54 | 52 |
| Seed treatment 2 oz DFU/cwt of seed | 111 | 1.22 | 0.0000016 | 109 | 112 | 111 | 112 |

Figure 15:
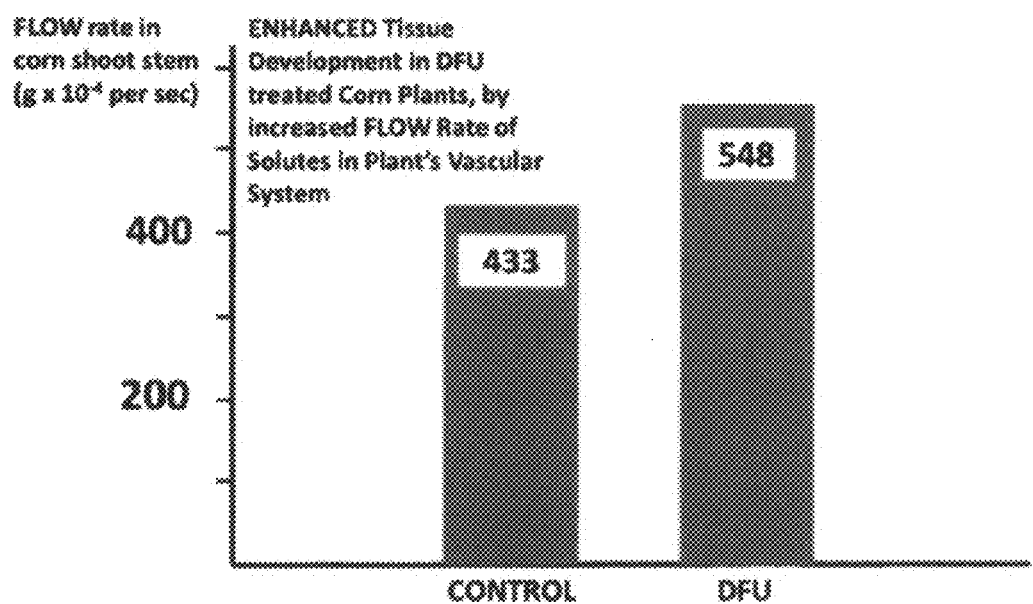
FIG. 15 is a graph illustrating enhanced tissue development in DFU treated corn plants (enhanced volumetric capacity of the stem). The graph further illustrates enhanced efficiency and volume flow of internal water and "growth" solutes.

Enhanced tissue development in DFU treated corn plants is illustrated by the experiment illustrated in FIG. 15. It has been also discovered that combining DFU and nitrogen fertilizer to the soil of a corn crop significantly enhances yield of the corn crop over simply using nitrogen fertilizer alone.

It has been further discovered that applying DFU to crop plants facilitates the efficiency of pesticides or herbicides or fungicides to enhance crop plant growth and crop productivity while not diminishing or suppressing the function of the pesticides, herbicides or fungicides.

It has also been discovered that greatly enhanced water use efficiency of up to 28% is achieved when crop plants have been treated with DFU.

Table 3 below illustrates the increased performance of herbicides and fungicides for crop plants by addition of DFU to the crops. Quadris™ fungicide (product of Syngenta Crop Protection, Inc.) was applied at the R1 stage of growth and gave a yield increase of 15 bushels per acre. DFU by itself increased soybean yields by 40 bushels per acre. DFU and Quadris applied together increased the yields by 52 bushels.

TABLE 3

| Treatment | Soybean Yield Bu/acre | Standard Deviation | T test vs Control P value | Rep 1 | Rep 2 | Rep 3 | Rep 4 |
|---|---|---|---|---|---|---|---|
| Control | 55.0 | 3.35 | | 53.0 | 57.2 | 50.6 | 59.1 |
| DFU @ 1 pt/acre | 95.1 | 4.49 | 1.47E−05 | 92.7 | 95.8 | 89.9 | 102 |
| Quadris @ recommended rate | 70.4 | 6.25 | 0.0016 | 65.4 | 72.9 | 63.9 | 79.5 |
| DFU together with Quadris at above rates | 107.0 | 3.39 | 0.00044 | 109.0 | 106.0 | 111 | 102 |

Table 4 below illustrates mineral use efficiency achieved with DFU applied to crop plants. A total of 180 lb of nitrogen fertilizer/acre, with ½ of nitrogen applied at V4 (forth leaf) and ½ at V7 (seventh leaf) as a side dress (3 inches to the side of the plant and 3 inches below the soil surface). The field corn cultivar DKC 66-96 was planted on Feb. 11, 2013 and harvested on Jul. 12, 2013. The harvested yield results reflect a 60.7% increase in efficiency of use of the available nitrogen mineral fertilizer by the DFU treatment of the seed.

TABLE 4

| Treatment | Average Yield bu per acre | Standard deviation | T test vs control p = % | Rep 1 Yield | Rep 2 Yield | Rep 3 Yield | Rep 4 Yield |
|---|---|---|---|---|---|---|---|
| Control Untreated | 112.6 | 9.3 | | 120.9 | 122.5 | 106.5 | 100.6 |
| Seed treat 2 oz/cwt V4 ½ pt V9 1 pt | 180.6 | 3.7 | 0.00098 | 175.5 | 188 | 178.7 | 185.1 |

Table 5 below illustrates the effect of foliar application of DFU applied at V4 (4th leaf stage of crop growth) at either the rate of ½ pt/acre along with the herbicide Round-Up™ herbicides on field corn. Both the control and the treatments also had 0.9 lb of ammonium sulfate applied along with the herbicide and di-formylurea (DFU). The field corn was planted in southern Texas on Mar. 3, 2012, at a population density of 35,000 plants per acre. The weed control was comparable and good with all the treatments. The large difference was in the harvestable yields of the di-formyl urea treated plants over the control which received the herbicide only.

TABLE 5

| Treatment | Yield Bu/acre | SD | T test vs control p = % | Yield increase bu/acre vs control | Yield % increase | Yield rep1 | Yield rep2 | Yield rep3 | Yield rep4 |
|---|---|---|---|---|---|---|---|---|---|
| Control | 209 | 2.6 | | | | 208 | 206 | 208 | 213 |
| V4 di-formylurea ½ pt/acre | 230 | 5.0 | 0.0013 | 29 | 13.9% | 227 | 232 | 224 | 237 |
| V4 di-formylurea 1 pt/acre | 254 | 6.7 | 0.00025 | 45 | 21.5% | 246 | 251 | 256 | 264 |

What is claimed is:

1. A method for preventing drowning of crop plants when flooded by excessive rain by applying diformylurea (DFU) in an open soil furrow at the time of crop seed sowing; wherein the applying of the DFU to the crop plants flooded by the excessive rain prevents the drowning of the crop plants and enhances the growth of the crop plants.

2. The method of claim 1 wherein the DFU is sprayed at a dose of 1 pint per acre to 1½ pints per acre over the seed and onto the soil of the open furrow below closure of the open furrow.

3. The method of claim 2 wherein pressure is applied to said closed furrow.

* * * * *